US00PP33170P2

(12) United States Plant Patent
Ren

(10) Patent No.: US PP33,170 P2
(45) Date of Patent: Jun. 15, 2021

(54) ***ECHINACEA* PLANT NAMED 'BALSOMSTOR'**

(50) Latin Name: ***Echinacea* x *hybrida***
Varietal Denomination: Balsomstor

(71) Applicant: Ball Horticultural Company, West Chicago, IL (US)

(72) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/007,809

(22) Filed: Aug. 31, 2020

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448; A01H 5/02
See application file for complete search history.

*Primary Examiner* — Keith O. Robinson
(74) *Attorney, Agent, or Firm* — Audrey Charles

(57) ABSTRACT

A new and distinct cultivar of *Echinacea* plant named 'Balsomstor', characterized by its single to semi-double type, deep reddish-orange colored inflorescences, medium green-colored foliage, and moderately vigorous, compact-upright growth habit, is disclosed.

1 Drawing Sheet

Latin name of genus and species of plant claimed: *Echinacea* x *hybrida.*

Variety denomination: 'Balsomstor'.

BACKGROUND OF THE INVENTION

The present invention relates to a new and distinct cultivar of *Echinacea* plant botanically known as *Echinacea* x *hybrida* and hereinafter referred to by the cultivar name 'Balsomstor'.

The new cultivar originated in a controlled breeding program in Elburn, Ill. during August 2013. The objective of the breeding program was the development of *Echinacea* cultivars with a single to semi-double inflorescence forms having imbricate ray florets and a well-branched, compact-upright growth habit.

The new *Echinacea* cultivar is the result of cross-pollination. The female (seed) parent of the new cultivar is the proprietary *Echinacea* x *hybrida* breeding selection coded E146, not patented, characterized by its double-type, medium orange-colored inflorescences, medium green-colored foliage, and moderately vigorous, compact-upright growth habit. The male (pollen) parent of the new cultivar is from a bulk pollen mix of eight proprietary *Echinacea* x *hybrida* breeding selections coded E58, E97, E105, and E113, not patented, characterized by their single-type, medium golden-orange and yellow colored inflorescences, medium green-colored foliage, and moderately vigorous, semi-upright growth habit. The new cultivar was discovered and selected as a single flowering plant within the progeny of the above stated cross-pollination during September 2014 in a controlled environment in Elburn, Ill.

Asexual reproduction of the new cultivar by in vitro shoot propagation since September 2014 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsomstor' as a new and distinct cultivar of *Echinacea* plant:

1. Single to semi-double type, deep reddish-orange colored inflorescences;
2. Medium green-colored foliage; and
3. Moderately vigorous, compact-upright growth habit.

Plants of the new cultivar differ from plants of the female and male parents primarily in having deeper reddish-orange colored inflorescences and in having a mixture of single and semi-double inflorescences.

Of the many commercially available *Echinacea* cultivars, the most similar in comparison to the new cultivar is SOMBRERO Flamenco Orange 'Balsomenco', U.S. Plant Pat. No. 25,523. However, in side-by-side comparisons, plants of the new cultivar differ from plants of 'Balsomenco' in at least the following characteristics:

1. Plants of the new cultivar have larger diameter inflorescences than plants of 'Balsomenco';
2. Plants of the new cultivar have a ray floret color that is a deeper reddish- orange color when fully open than plants of 'Balsomenco'; and
3. Plants of the new cultivar have more ray florets per inflorescence than plants of 'Balsomenco'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs may differ slightly from the color values cited in the detailed description, which accurately describes the colors of 'Balsomstor'. The plants were approximately six months old. The plants were grown in one-gallon containers for approximately 14 weeks in an outdoor nursery in West Chicago, Ill. Plants were given two pinches prior to transplant.

DETAILED BOTANICAL DESCRIPTION

Figure 1:
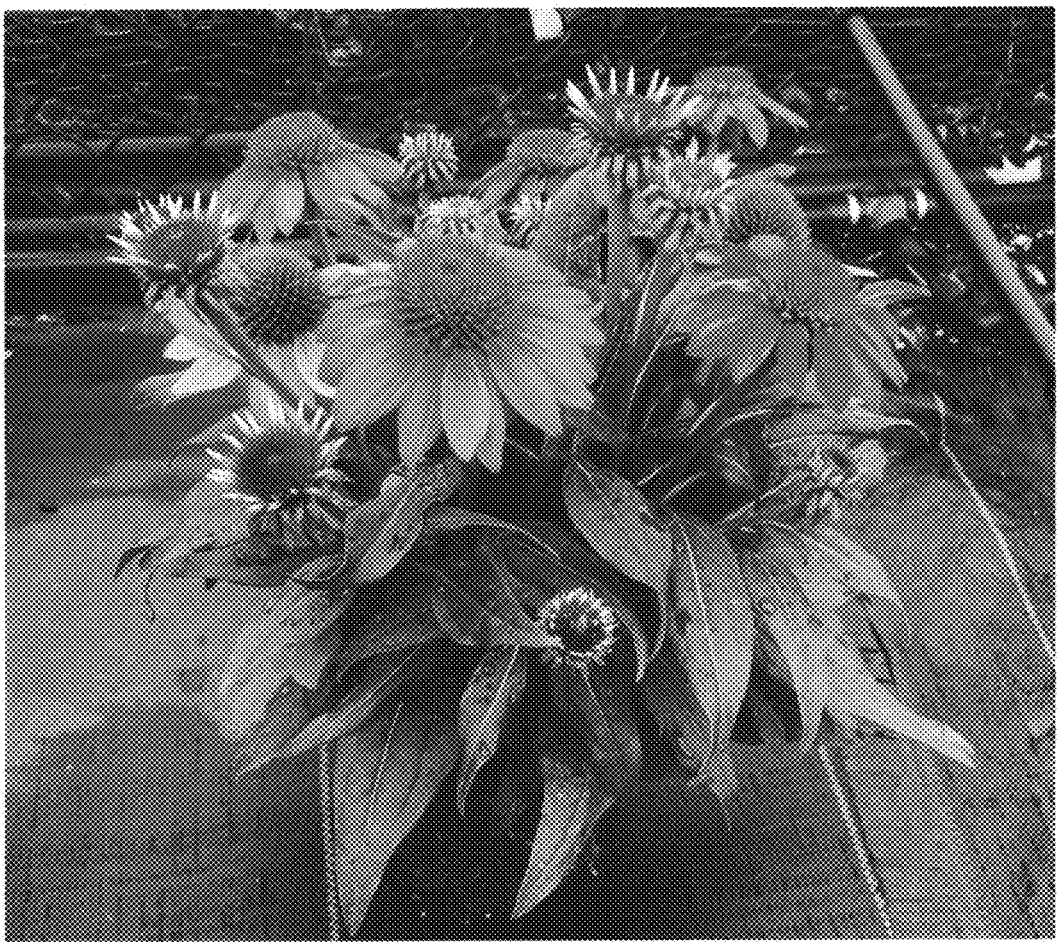
FIG. 1 illustrates a side view of the overall growth and flowering habit of 'Balsomstor'.
Figure 2:
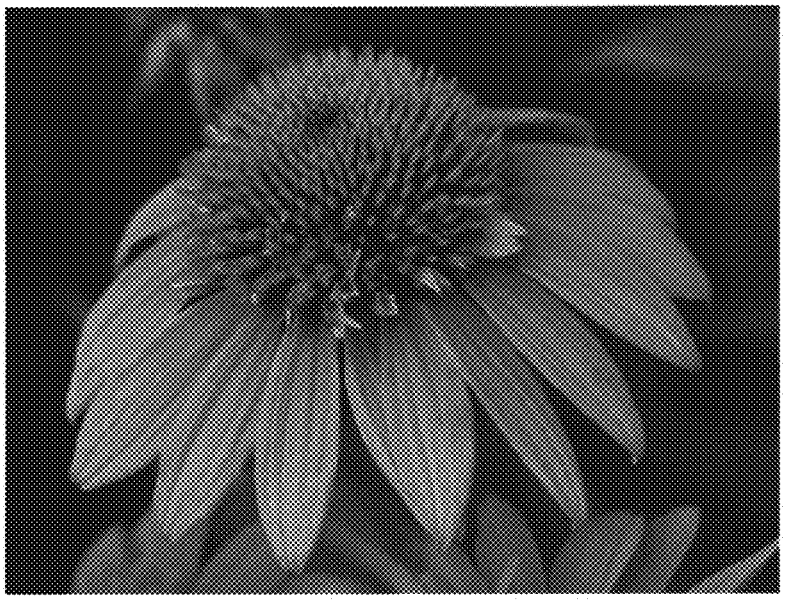
FIG. 2 illustrates a close-up view of an individual inflorescence of 'Balsomstor'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2020 under natural light conditions in Naperville, Ill.

The following descriptions and measurements describe approximately six-month old plants produced from in vitro plantlets and grown under conditions comparable to those used in commercial practice. The plants were grown in one-gallon containers for approximately 14 weeks in an outdoor nursery in West Chicago, Ill. Plants were given two pinches prior to transplant. Prior to transplant plants were grown in a 50-cell liner in a poly-covered greenhouse in West Chicago, Ill. Greenhouse temperatures ranged from an average high of 69.3° F. (20.7° C.) to an average low of 63.6° F. (17.6° C.), and supplemental lighting was provided daily for five hours during short days. Measurements and numerical values represent averages of typical plants.

Botanical classification: *Echinacea* x *hybrida* 'Balsomstor'.

Parentage:

*Female parent*.—Proprietary *Echinacea* x *hybrida* breeding selection coded E146, not patented.

*Male parent*.—A bulk pollen mix of eight proprietary *Echinacea* x *hybrida* breeding selections coded E58, E97, E105, and E113, not patented.

Propagation:

*Type*.—In vitro propagation is preferred, divisions are possible.

*Time to initiate roots in vitro*.—Approximately 30 days at 18° C.

*Time to produce a rooted plantlet in summer*.—Approximately 30 days at 18° C.

*Root description*.—Fine, fibrous.

*Rooting habit*.—Moderate density, moderate branching.

Plant description:

*Commercial crop time*.—Approximately 10 to 12 weeks from a rooted tissue culture plantlet to finish in a 15 cm container.

*Growth habit and general appearance*.—Herbaceous perennial, moderately vigorous, compact-upright.

*Hardiness*.—USDA Zone 4b (−25° F. to −20° F./−32° C. to −29° C.).

*Size*.—Height from soil level to top of plant plane: Approximately 29.5 cm. Width: Approximately 39.0 cm.

*Branching habit*.—No lateral branching, flowering stems grow from base. Quantity of main stems per plant: Approximately 4.

*Stems*.—Strength: Very strong. Aspect: Nearly erect. Shape: Rounded. Length to base of inflorescence: Approximately 13.0 cm. Diameter: Approximately 7.0 mm to 9.0 mm. Length of central internode: Approximately 3.0 cm. Texture: Densely pubescent with short strigose hairs. Color of young and mature stems: 144A to 144B with small streaks of 137A.

Foliage description:

*General description*.—Form: Simple. Arrangement: Alternate.

*Leaves*.—Aspect: Perpendicular to stem, subtending with age. Shape: Narrowly ovate to lanceolate. Margin: Entire, slightly undulate. Apex: Acute. Base: Attenuate. Venation pattern: Pinnate. Length of mature leaf: Approximately 10.0 cm. Width of mature leaf: Approximately 4.5 cm. Texture of upper surface: Dull, moderately rugose, moderately pubescent with short strigose hairs. Texture of lower surface: Moderately pubescent with short strigose hairs. Color of upper surface of young and mature foliage: Closest to NN137A with venation of 145C. Color of lower surface of young and mature foliage: Closest to 147B with venation of 145C.

*Petiole*.—Shape: V-shaped. Length: Approximately 4.0 cm to 10.0 cm. Diameter: Approximately 3.0 mm to 5.0 mm. Texture of upper surface: Glabrous. Texture of lower surface: Sparsely covered with very short strigose hairs. Color of upper and lower surfaces: 145B to 145C.

Flowering description:

*Flowering habit*.—'Balsomstor' is freely flowering blooming from late spring through late summer under outdoor growing conditions.

*Lastingness of individual inflorescence on the plant*.—Approximately 3 weeks.

Inflorescence description:

*General description*.—Type: Solitary, daisy, composite. Persistent. Shape: Conical. Aspect: Facing upward. Arrangement: Terminal, held upright on strong peduncles. Fragrance: Faintly sweet. Quantity per plant: Approximately 7. Height: Approximately 4.0 cm. Diameter: Approximately 9.5 cm.

*Peduncle*.—Strength: Strong. Aspect: Erect to approximately 45° from vertical. Length: Approximately 12.0 cm. Diameter: Approximately 5.0 mm to 7.0 mm. Texture: Densely pubescent with short strigose hairs. Color: 144A to 144B with small streaks of 137A.

*Bud*.—Quantity per plant: Approximately 12. Shape: Flattened globular with immature ray florets nearly erect. Length: Approximately 1.5 cm. Diameter: Approximately 1.8 cm. Color: Outer ray florets of 154D tinted with 186B with bud center of 143A.

*Ray florets*.—Quantity per inflorescence: Approximately 20. Arrangement: In a single whorl, slightly imbricate. Aspect: Perpendicular to disc, subtending with age, twisting absent. Shape: Elliptic. Appearance: Matte. Margin: Entire. Apex: Three acute tips. Base: Attenuate. Length: Approximately 4.2 cm. Width: Approximately 1.4 cm. Texture of upper surface: Glabrous, ribbed longitudinally. Texture of lower surface: Sparsely pubescent, ribbed longitudinally. Color of upper surface when first open: 44A with 45A at base. Color of lower surface when first open: 186C to 186D. Color of upper surface when fully open: 34A to 34B with an overlay of N34A at base, with senescence fades to 168A to 168C. Color of lower surface when fully open: Closest to 186D with 155A.

*Disc florets*.—Disc diameter: Approximately 4.0 cm. Quantity per inflorescence: Approximately 240. Arrangement: Spirally arranged in center of inflorescence. Shape: Tubular. Margin of free portion: Entire. Apex: Five acute tips. Base: Fused into a tube. Length: Approximately 1.1 cm, when semi-double the outermost rows can develop to approximately 1.5 cm and up to approximately 2.5 cm. Diameter: Approximately 2.0 mm, when semi-double approximately 5.0 mm. Texture: Glabrous. Color of upper or inner surface when first and fully open: 146D with N25A and 187A at tips, when semi-double 34A to 34B. Color of lower or outer surface when first and fully open: 146D with 187A at tips and base of NN155D, when semi-double 186A to 186B.

*Receptacle*.—Shape: Conical. Height: Approximately 1.5 cm. Diameter: Approximately 1.5 cm. Color: 155D.

*Phyllaries*.—Quantity per inflorescence Approximately 48. Arrangement: In multiple whorls. Appearance: Dull, stiff. Shape: Narrowly ovate to lanceolate, strongly curved towards the peduncle. Margin: Entire, ciliate. Apex: Acute. Base: Truncate. Length: Approximately 1.1 cm to 1.7 cm. Width: Approximately 3.0 mm to 4.0 mm. Texture of upper or inner surface: Glabrous. Texture of lower or outer surface: Sparsely pubescent with short strigose hairs. Color of upper surface: 137A. Color of lower surface: 137B.

*Receptacle spines*.—Number of spines per disc: Approximately 240. Shape: Acicular. Length: Approximately 1.6 cm. Width at widest point: Approximately 2.0 mm. Apex: Acute. Base: Truncate. Texture: Glabrous. Color: Apex of 167B with tip of 187A, mid-section of 146D, and base of NN155D.

*Reproductive organs*.—Androecium: Present on disc florets only. Stamen quantity: 5 per floret. Anther shape: Oblong, basifixed. Anther length: Approximately 3.0 mm. Anther color: Closest to 200C. Filament length: Approximately 2.0 mm. Filament color: 155D. Pollen amount: Abundant. Pollen color: 17A. Gynoecium: Present on disc florets only. Pistil quantity: 1 per floret. Pistil length: Approximately 1.1 cm. Stigma shape: Bifid. Stigma length: Approximately 2.0 mm. Stigma color: 187A. Style length: Approximately 6.0 mm. Style color: 145D. Ovary length: Approximately 4.0 mm. Ovary color: NN155D.

Seed and fruit production: Neither seed nor fruit production has been observed.

Disease and pest resistance: Resistance to pathogens and pests common to *Echinacea* has not been observed.

What is claimed is:

1. A new and distinct cultivar of *Echinacea* plant named 'Balsomstor', substantially as herein illustrated and described.

* * * * *